(12) United States Patent
Jones et al.

(10) Patent No.: US 7,027,931 B1
(45) Date of Patent: Apr. 11, 2006

(54) SYSTEM FOR STATISTICAL ANALYSIS OF QUALITY CONTROL DATA

(75) Inventors: Jeffrey A. Jones, Plaistow, NH (US); David W. Hatch, Hudson, MA (US); Nancy D. Hallock, Pittsford, CA (US); Sundar Balasuryan, Lexington, MA (US)

(73) Assignee: Bionostics, Inc., Devens, MA (US)

( * ) Notice: Subject to any disclaimer, the term of this patent is extended or adjusted under 35 U.S.C. 154(b) by 250 days.

(21) Appl. No.: 09/793,371

(22) Filed: Feb. 26, 2001

Related U.S. Application Data

(60) Provisional application No. 60/184,621, filed on Feb. 24, 2000.

(51) Int. Cl.
*G01N 33/48* (2006.01)
*G01N 1/00* (2006.01)
*G01N 15/00* (2006.01)
*G06G 7/48* (2006.01)
*B01J 8/00* (2006.01)

(52) U.S. Cl. .......................... 702/19; 703/11; 422/50; 422/68.1; 422/129

(58) Field of Classification Search ............ 422/50, 422/68.1, 129; 435/6, 7.1; 702/19; 703/11
See application file for complete search history.

(56) References Cited

U.S. PATENT DOCUMENTS

| | | | | |
|---|---|---|---|---|
| 4,858,154 | A * | 8/1989 | Anderson et al. | 702/81 |
| 5,608,874 | A * | 3/1997 | Ogawa et al. | 709/246 |
| 5,764,542 | A * | 6/1998 | Gaudette et al. | 702/179 |
| 5,845,285 | A * | 12/1998 | Klein | 707/101 |
| 5,937,364 | A * | 8/1999 | Westgard et al. | 702/83 |

OTHER PUBLICATIONS

David Plaut & Glenn Whitehair, Benefits of New LabLink QC/QAP System for Cos-effective Data Management with Advanced Features for the Laboratory, CLMA Industry Workshop, Toronto, Canada, Sponsored by Dade International, Inc., pp. 1-4, Aug. 17, 1997.

L. Scott, Dade International Inc., "Quality Monitor Technical Requirments Specification", Rev. Number: 316, pp. 59 and 60, Mar. 12, 1996.

Harald Iverson and Venie Valdivia, "Quality Assurance Program Statistical Design Requirments", Dade International Inc., Miami, Florida, Rev. Number 8, pp. 1-30, Revision: 1.02, Revision Date: Feb. 20, 1996.

* cited by examiner

*Primary Examiner*—Mary K. Zeman
*Assistant Examiner*—Anna Skibinsky
(74) *Attorney, Agent, or Firm*—Hamilton, Brook, Smith & Reynolds, P.C.

(57) ABSTRACT

A statistical database system can improve error checking of quality control data used to measure the performance of quantitative analysis equipment. The quality control data can be delivered to a centralized database, wherein the database is linked to error checking functions. Data delivery can be flexible, allowing input via scanning, operator keyed summary data, operator keyed raw data, analyzer direct download, Internet-delivered summary data and Internet-delivered raw data. The received quality control data can be verified against specific lot and analyzer parameters, and data falling outside of these specified ranges can be excluded from a peer group. Excluded data can be verified against original submitted data, and excluded data can then appear on final reports. The quality control data can also be entered directly into the database and a peer group report can then be generated. The quality control data is processed in real time with the data entry and the reports are viewable in real time.

53 Claims, 9 Drawing Sheets

Your Company LOGO HERE

YOUR STATISTICAL SERVICES PROGRAM

Report Period: JUNE 1999

COMMUNITY MEMORIAL HOSPITAL
123 Hospital Drive
Anywhere
MA 011234
Attn: Respiratory Therapy Date Printed: July 16, 1999
Product: Prod Name
Instrument ID: Analyser #1
Instrument Model: RADIO AU 500
Date Submitted: Summary

| | Level | Lot # | N ACC. Req. | JUNE 1998 STATISTICS | | | | | CUMULATIVE STATISTICS | | | | | PEER GROUP STATISTICS RADIOMETER MODELS EXCEPT OSMs | | | | |
|---|---|---|---|---|---|---|---|---|---|---|---|---|---|---|---|---|---|---|
| | | | | N | Mean | SD | 2 SD Range | CV% | SDI | N | Mean | SD | 2 SD Range | CV% | SDI | M | Mean | SD | CV% | CV1 |
| pH | 1 | 1001 | 30 0 | 0 | 7.125 | 0.005 | 7.115 - 7.135 | 1.14 | -0.21 | 60 | 7.125 | 0.005 | 7.116 - 7.134 | 1.03 | -0.32 | 520 | 7.126 | 0.005 | 1.08 | 1.056 |
| | 2 | 2002 | 30 0 | 0 | 7.397 | 0.005 | 7.387 - 7.407 | 1.14 | 0.54 | 60 | 7.396 | 0.005 | 7.306 - 7.406 | 1.17 | 0.31 | 520 | 7.395 | 0.004 | 0.99 | 1.152 |
| | 3 | 3003 | 30 0 | 0 | 7.598 | 0.005 | 7.588 - 7.608 | 1.14 | 0.40 | 60 | 7.599 | 0.005 | 7.590 - 7.608 | 1.05 | 0.56 | 520 | 7.596 | 0.006 | 1.35 | 0.844 |
| pCO2 | 1 | 1001 | 30 0 | 0 | 70.00 | 1.50 | 67.00 - 73.00 | 2.14 | -0.87 | 60 | 69.90 | 1.35 | 67.20 - 72.60 | 1.93 | -0.96 | 520 | 70.96 | 1.10 | 1.55 | 1.38 |
| | 2 | 2002 | 30 0 | 0 | 40.00 | 1.00 | 38.00 - 42.00 | 2.50 | -0.43 | 60 | 39.95 | 0.97 | 38.01 - 41.88 | 2.42 | -0.48 | 520 | 40.43 | 1.01 | 2.49 | 1.00 |
| | 3 | 3003 | 30 0 | 0 | 20.00 | 1.00 | 18.00 - 22.00 | 5.00 | 0.12 | 60 | 19.90 | 0.80 | 18.31 - 21.49 | 4.00 | -0.02 | 520 | 19.97 | 0.69 | 3.48 | 1.44 |
| pO2 | 1 | 1001 | 30 0 | 0 | 100.00 | 3.00 | 94.00 - 106.00 | 3.00 | -0.41 | 60 | 99.90 | 2.74 | 94.42 - 105.38 | 2.74 | -0.46 | 520 | 100.77 | 1.86 | 1.85 | 1.62 |
| | 2 | 2002 | 30 0 | 0 | 70.00 | 2.50 | 65.00 - 75.00 | 3.57 | -0.45 | 60 | 69.94 | 2.35 | 65.24 - 74.63 | 3.36 | -0.50 | 520 | 70.66 | 1.47 | 2.07 | 1.72 |
| | 3 | 3003 | 30 0 | 0 | 40.00 | 1.50 | 37.00 - 43.00 | 3.75 | 0.19 | 60 | 39.93 | 1.36 | 37.20 - 42.65 | 3.41 | 0.10 | 520 | 39.84 | 0.82 | 2.07 | 1.81 |

Notes
1 "Rej." ARE TEST VALUES IN EXCESS OF +/-3SD FROM INSTRUMENT MEAN "Rej." DATA HAS BEEN EXCLUDED FROM THE CURRENT MONTH AND ALL CUMULATIVE STATISTICS
2 ONLY THOSE LOTS FOR WHICH THE CURRENT MONTH DATA HAS BEEN SUBMITTED ARE INCLUDED IN THE SUMMARIES
3 CV% FOR pH HAS BEEN CALCULATED ON THE BASIS OF H+ ION CONCENTRATION (nmol/L)
4 UNLESS OTHERWISE INDICATED, ALL UNITS FOR pCO2 AND pO2 ARE REPORTED IN mmHg AND ALL ELECTROLYTA VALUES ARE REPORTED IN mmol/l
5 HIGHLIGHTED DATA INDICATES THAT EITHER THE MEAN OR SD VALUE IS OUTSIDE OF THE MANUFACTURES PACKAGE INSERT RANGES. THIS DATA HAS BEEN EXCLUDED FORM THE PEER GROUP Page: 1

ANY OEM CUSTOMER   123 Main Street, Anytown US 123456   Tel 555 555 5252   Sales 800 555 5252   Fax 555 555 1212

SYSTEM FOR STATISTICAL ANALYSIS OF QUALITY CONTROL DATA

RELATED APPLICATION

This application claims the benefit of U.S. Provisional Application No. 60/184,621, filed on Feb. 24, 2000 by Jones and Hatch, the entire teachings of which are incorporated herein by reference.

BACKGROUND

Quantitative analysis equipment is used to analyze a sample substance (analyte) to determine its chemical composition. The equipment is generally specialized to measure certain chemicals or to analyze specific substances. The equipment includes chemical analysis equipment used in the chemical industry and medical diagnostic equipment in the medical industry.

In the medical industry, for example, diagnostic equipment is used to analyze patient fluid samples, such as blood samples. Such medical diagnostic equipment can measure properties such as blood gases, electrolytes, and glucose levels. Based on the analysis, physicians and other health care providers diagnose illnesses and implement treatments. To obtain effective treatment, it is therefore important that the medical diagnostic equipment function correctly and provide an accurate analysis.

In an effort to maintain accuracy, the analysis equipment should be routinely tested. Typically, quality control samples of known compositions are analyzed by the equipment. Based on the equipment's measurements of the quality control sample, the equipment may be declared to be operating within or outside its acceptable range of operation. This decision, however, must typically be based on accurate quality control data entry. In reality, human data entry errors can adversely affect the decision process.

Although raw data measurements of quality control samples can be automatically validated by each individual piece of equipment, statistical analysis of the equipment's performance over time relies on cumulative quality control measurement data. This cumulative data typically includes measurements, by the particular unit, of quality control samples over time. The statistics from any one piece of equipment may also be compared with selected groups of similar equipment, such as peer groups. Again, human data entry errors can make such comparisons unreliable.

Furthermore, error checking within peer groups typically involves the use of broad error checking parameters based solely upon the analyte being tested. Typically, a peer analysis program requires delivery of quality control data to a dedicated remote technology for error checking. This dedicated remote technology may include a database having error functionality.

The quality control data can be delivered electronically or manually inputted. Typically, the quality control data is delivered in the form of internal summary data or internal raw data (for example, Levy-Jennings charts) that is manually typed into the database. The quality control data is then checked against global analyte parameters.

Results of the data checking are sent to a central database where the results are printed and manually checked for obvious errors. Typically, outlier data is either included in the report and the database, or excluded entirely.

SUMMARY

The prior art methods of peer group analysis do not take into account variances between lots of analytes or between instruments. Furthermore, those methods do not use error checking in any comprehensive manner within a statistical database, because the quality control data that forms the basis of comparison can easily be corrupted by erroneous entries. This is due, in part, to the fact that broad parameters cannot be used as an accurate basis for the exclusion of outlier data. Without such exclusion, real-time, online reports are not possible without risking erroneous reports to the client or delaying reporting until separate off-line checks are performed. Finally, these methods provide no verification of outlier data.

Embodiments of the invention facilitate the integrity of quality control data, especially peer group data. Particular embodiments of the invention facilitate the detection and identification of outlier data in quality control measurements. In addition, the outlier data can be corrected for inclusion into quality control data statistics.

A particular statistical analysis system can feature analyte-specific, lot-specific and analyzer-specific error checking parameters, a centralized database of peer grouped information, real-time data entry into the centralized database and an analysis using the centralized database. The centralized database can include data from all input sources that can be accessed for information pertaining to any given peer group.

A particular embodiment includes a computer system for detecting errors in the quality control testing of a quantitative analyzer. The particular computer system includes a database having stored therein an expected statistical data value representing the composition of a known sample of an analyte, such as concentration of the analyte per unit of a sample, for a plurality of analyzers. The expected statistical data value can be specific to a particular control lot of the sample. The particular computer system can also include an inputted statistical data value for representing the composition of the known sample as measured by an analyzer under test. A module can then compares the inputted value with the expected value. The inputted data can be manually input by a user or electronically input by a computer or an analyzer.

In the particular computer system, the database can be shared between a plurality of analyzers under test. The database can also be a central database controlled by a server. The database can further store cumulative statistical data for a plurality of tests of the analyzer under test. The database can be coupled to a public-access or private-access communication medium, including a Local Area Network (LAN) or Wide Area Network (WAN), such as the Internet.

The inputted data value can represent a summary statistical value, such as a mean value, of the measured composition from a plurality of measurements or a raw measured value of the measured composition. The module of the particular computer system can include an error reporting function to identify an inputted statistical data value that is inconsistent with the expected statistical data value. The error reporting function can permit the acceptance of the inconsistent inputted value.

A more particular embodiment is a computer system for quality control testing of a chemical analyzer. The computer system includes a test analyte having an expected chemical composition and an analyzer capable of measuring the chemical composition of the test analyte. A computer is coupled to a database storing statistical data for the test analyte, for a plurality of analyzers, including expected statistical data representing the expected chemical composition. A data collection module receives data representing a measured composition of the test analyte into the computer. An error checking module in the computer compares the received data with the expected chemical composition.

In accordance with this more particular embodiment, the expected statistical data can be specific to a control lot of the test analyte. The expected statistical data can also be specific to a particular analyzer model. The statistical data can include a mean data value and a standard deviation data value. The database can also store cumulative statistical data for the analyzer.

The data collection module can receive data from a communication network coupled between the computer and the analyzer. The received data can be electronically transmitted over the communication network by the analyzer. The received data can also be electronically transmitted over the communication network by a remote computer coupled to the analyzer. The received data can also be manually inputted into the database.

The error checking module can include an error reporting function for reporting received data outside a range of expected data for the expected chemical composition to a user. The error reporting function can be capable of receiving a corrected data value from the user for entry into the database. The error checking module can process data in real time with the data collection module.

The more particular computer system can further include a reporting module for generating query reports. The reporting module can be capable of generating reports based on a peer group selected by a user. The query report can be accessible in real time, such as being accessible over a communication network, including posting on an Internet web page or another browser-readable file.

In accordance with another particular embodiment, a computer system for quality control testing of a chemical analyzer can include a test analyte having an expected chemical composition and an analyzer under test capable of measuring the chemical composition of the test analyte.

A database can store, for a plurality of analyzer models, statistical data for the test analyte. This statistical data can include expected statistical data representing the expected chemical composition, where the expected statistical data is specific to the analyzer model and to a control lot of the test analyte. The statistical data can include a mean data value and a standard deviation data value. The database can also store cumulative statistical data for a plurality of analyzers, including the analyzer under test. A computer can be coupled to the database.

A data collection module can receive data representing a measured composition of the test analyte into the computer. The data can be received from a manual user input. The data collection module can also receive data from a communication network coupled between the computer and the analyzer under test. The received data can electronically transmitted over the communication network by the analyzer under test or by a remote computer. The data can be entered into the remote computer manually or via an electronic link with the analyzer under test.

An error checking module in the computer can compare the received data with the expected chemical composition. The error checking module can detect a human-induced error in the received data. The error checking module can also include an error reporting function for reporting received data outside a range of expected data for the expected chemical composition to a user. The error reporting function can be capable of receiving a corrected data value from the user for entry into the database. The error checking module can processes the received data in real time with the data collection module.

A report generation module in the computer can generate reports from the statistical data stored in the database. The reporting module is capable of generating reports based on a peer group selected by a user. The report can be available in real time. In particular, the report is accessible over a communication network.

Furthermore, the error checking module can support the expected chemical composition having a first unit of measure and the measured chemical composition having a second unit of measure. The error checking module can then convert the first unit of measure to the second unit of measure. In that case, the generated report can use the second unit of measure.

In accordance with yet another particular embodiment, a system for detecting errors in the quality control testing of a quantitative analyzer can include an analyzer, a communication system, and a computer.

The analyzer can measure the composition of a known sample of quality control material. In particular, the analyzer is a chemical analyzer.

The communication system can forward the measured composition to a statistical analysis database, which compares the measured composition with an expected composition. The communication system can interface to a communication medium, which can be a Local Area Network (LAN) or a Wide Area Network (WAN), such as the Internet. In that case, the computer or the analyzer can transmit the measured composition over the communication medium.

The computer can facilitate user review of the comparison from the communication medium. In particular, the computer can facilitate review of a query report generated from the statistical analysis database. The query report can include statistical data from a plurality of analyzers, such as a peer group of analyzers. The report can exclude a measurement of the quality control material that is inconsistent with the expected composition or can include a measurement of the quality control material that is inconsistent with the expected composition. The report can also be viewable in real time.

The measured composition can include a plurality of measurements of the quality control material. The measurements can be forwarded via the communication system as raw data or as summary data. In addition, the measured composition can be entered into the computer for transmission over the communication medium.

Still another embodiment of the invention includes a method of detecting errors in the quality control testing of a quantitative analyzer. In an analyzer, the composition of a known sample of quality control material is measured. The measured composition can include a plurality of measurements of the quality control material. In a particular embodiment, the analyzer is a chemical analyzer.

Using a communication system, the measured composition can be forwarded to a statistical analysis database, which compares the measured composition with an expected composition and generates a report. The measurements can be forwarded through the communication system as raw data or summary data. A computer can be coupled to a communication medium for facilitating a review of the report.

The communication system can include an interface to the communication medium. The measured composition can then be transmitted by the computer through the communication medium. The analyzer can also be coupled to the communication medium, and the measured composition can be transmitted by the analyzer through the communication medium.

The generated report can include statistical data from a plurality of analyzers. The plurality of analyzers can, in particular, include a peer group of analyzers. The report can include or exclude a measurement of the quality control material, as controlled by a user, that is inconsistent with the expected composition. The report can be viewable in real time.

The various embodiments of the system can provide the advantages of real-time reports based on all input sources within a single peer group. The system can allow objective, online determinations about the validity of data. The validity determinations are specific to the analyte control lot or analytes and analyzer. The comprehensive error checking can ensure the integrity of the peer group, allowing processing of real-time reports online.

BRIEF DESCRIPTION OF THE DRAWINGS

The foregoing and other objects, features and advantages of the invention will be apparent from the following more particular description of particular embodiments of a system for statistical analysis of analytes and instrumentation data, as illustrated in the accompanying drawings in which like reference characters refer to the same parts throughout the different views. The drawings are not necessarily to scale, emphasis instead being placed upon illustrating the principles of the invention.

FIG. 8 illustrates an example report generated by the reporting function 600 of FIG. 7.

DETAILED DESCRIPTION

In accordance with a particular embodiment of the invention, a statistical database system can improve error checking of chemical analysis equipment. The data can be delivered to a centralized database, wherein the database is linked to error checking functions. Data delivery can be flexible, allowing input via scanning, operator-keyed summary data, operator keyed raw data, analyzer direct download, Internet-delivered summary data and Internet-delivered raw data. The received data can be verified against specific lot and analyzer parameters, and data falling outside of these specified ranges can be excluded from a peer group. Excluded data can be verified against original submitted data, and excluded data can then appear on final reports. The data can also be entered directly into the database and a peer group report can then be generated.

Figure 1:
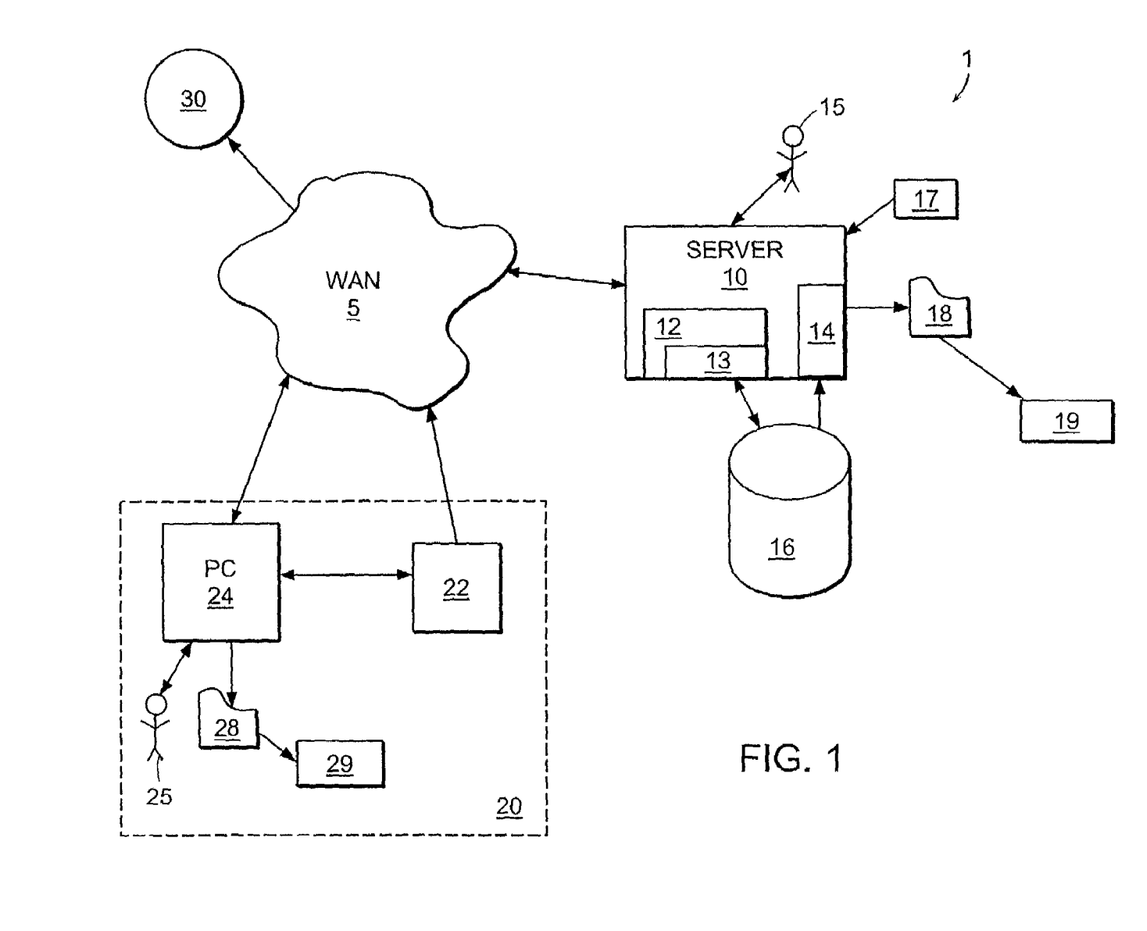
FIG. 1 is a block diagram of a particular statistical analysis system.

FIG. 1 is a block diagram of a particular statistical analysis system. As shown, the system 1 includes a quality control server 10 in communication with a wide area network (WAN) 5 using suitable communication protocols. In particular, the WAN 5 can be a public-access communications network, such as the Internet. It should be understood that the server 10 can include a plurality of computers, such as a clustered server. The system can also be embodied in a peer-to-peer network architecture. It should also be understood that a Local Area Network (LAN) or other suitable public or private communication mediums can be substituted for the WAN 5.

The quality control server 10 includes a data collection module 12, an error checking module 13, and a reporting module 14 that interfaces with quality control data stored in a database 16. The data can be received from the Internet 5, from a user's 15 input, or scanned from paper forms (e.g., Levy-Jennings) using a scanner 17. The report module 14 creates reports 18 that can be printed on a printer 19, or otherwise delivered to a recipient—including electronic mail or other electronic delivery. In particular, the electronic delivery makes the report available to clients in real time, such as via an Internet web page or other browser-accessible files.

An example customer site 20 is shown in communication with the WAN 5 using suitable communication protocols. The customer site includes a medical diagnostic unit or analyzer 22, which can be directly connected to provide quality control data over the Internet 5 to the quality control server 10. Also shown is a client computer 24 operated by a client user 25. The data can be manually inputted by the client user 25. A printer 29 can be used to print reports 28.

A third-party client 30 is also shown in communication with the Internet 5. The third party 30 can be provided with reports generated from the database 16. The third party 30 can be an equipment manufacturer or a regulatory agency, for example.

A specific concern addressed by the system 1 is the maintenance of data integrity. It is recognized that when the data cannot be trusted, the results are suspect. The statistical analysis system 1 can provide customers with prompt and accurate database services. To that end, it should be understood that the system 1 can include further services that are not illustrated, including transaction logs, backup services, and audit reporting functions.

Figure 2:
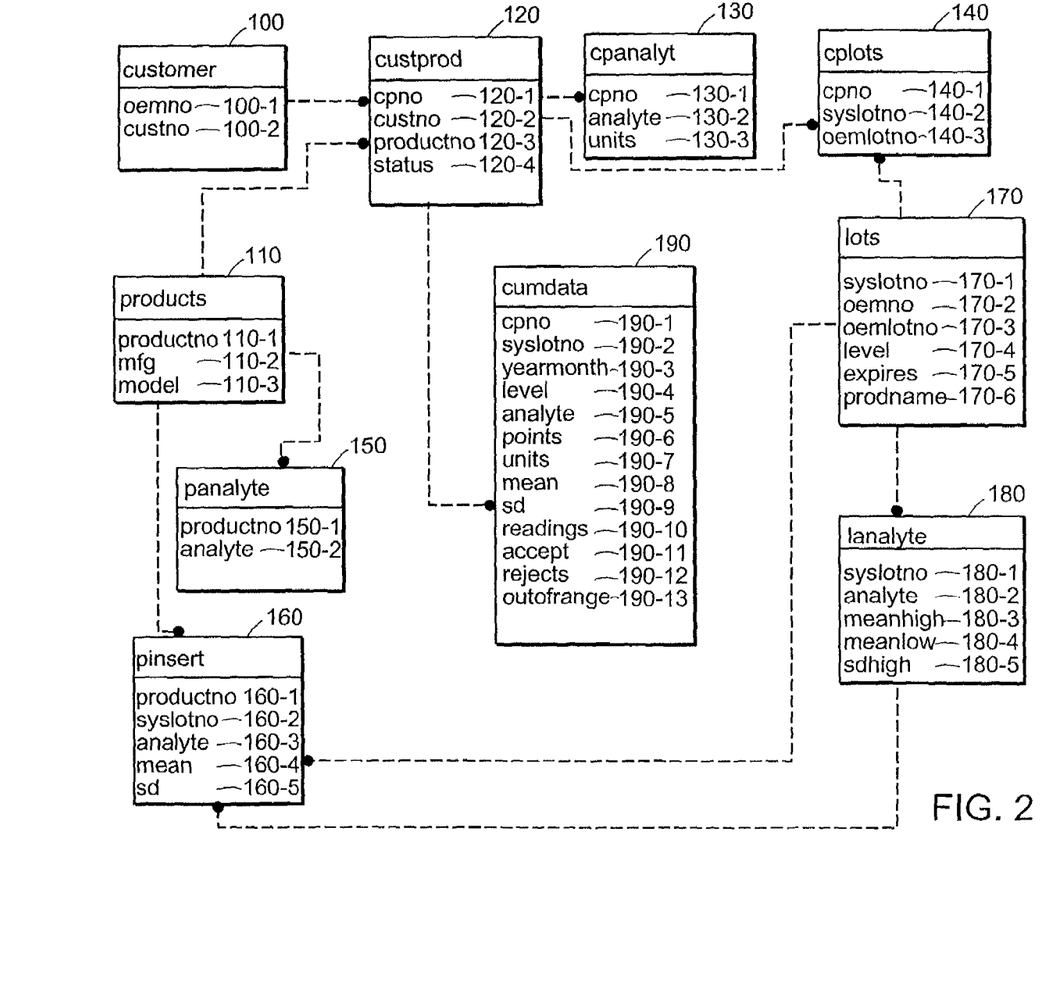
FIG. 2 is a diagram of a particular relational database stored in the central database 16 of FIG. 1.

FIG. 2 is a diagram of a particular relational database stored in the central database 16 of FIG. 1. The database 16 includes a customer table 100, a customer product table 120, a customer product analyte table 130, and a customer product lot table 140. Also shown is a product table 110, a product analyte table 150, a package insert table 160, a lots table 170, and a lot analyte table 180. Cumulative data is stored in a cumulative data table 190. Although not shown, all analyte data can be stored in a master analytes table.

The customer table 100 uniquely identifies each customer. As shown, the customer table 100 includes two fields: an original equipment manufacturer (OEM) number field 100-1 and a customer number field 100-2. The customer table is linked forward to customer product table 120 via the customer number fields 100-2.

The product table 110 stores the analyzer's manufacturer's information. The machine is identified by an analyzer product number field 110-1, a manufacturer's identification field 110-2, and a model identification field 110-3. This table is linked forward to the customer product table 120, the product analyte table 150, and the package insert table 160 via the product number field 110-1.

The customer product table 120 identifies all of the analyzers information. The table includes a customer product number field 120-1, a customer number field 120-2, an analyzer product number field 120-3, and a status field 120-4. The customer product number 120-3 is a unique number that is assigned at enrollment in the system, and should not be confused with the product number, which is an identifier for a specific make and model of analyzer. The customer product table 120 is linked back with the customer table via the customer number field 120-2 and the products table 110 via the product number field 120-3. The customer product table 120 is linked forward to the customer product analyte table 130, the customer product lot table 140, and the cumulative data table 190 via the customer product number field 120-1.

The customer product analyte table 130 identifies the analytes associated with a particular customer product. The table includes a customer product number field 130-1, an analyte identification field 130-2, in a units identification field 130-3. The customer product analyte table 130 is linked back with the customer product table 120 via the customer product number field 130-1.

The customer product lot table 140 identifies the particular analyte lots analyzed by the customer product. The table includes a customer product number field 140-1, a system lot number field 140-2, and an OEM lot number field 140-3. The customer product lot table 140 is linked back with the customer product table 120 via the customer product number field 140-1 and the lots table 170 via the system lot number field 140-2.

The product analyte table 150 stores the analytes that each respective analyzer is capable of reporting. It thereby associates a particular analyte with a particular product. The table includes a product number field 150-1 and an analyte identification field 150-2. The product analyte table 150 is linked back with the products table 110 via the product number field 150-1.

The system's error checking capabilities rely on the use of package insert ranges. These are the expected ranges that are included in each package of quality control material. These ranges are determined by Quality Assurance personnel and are based upon field data, test data, and bias formulations. Each insert sheet gives the expected range for each analyte based on the make and model of the analyzer. The sheets are intended as a starting point for laboratory personnel.

The package insert table 160 is the main table used in the error checking process. The table stores the expected data from the package insert sheets. The table includes a product number field 160-1, a system lot number field 160-2, an analyte identification field 160-3, a mean value field 160-4, and a standard deviation field 160-5. The mean and standard deviation values are used in the error detection process. The package insert table 160 links back with the products table via the product number field 160-1 and with the lots table 170 and lot analyte table 180 via the system lot number field 160-2.

The lots table 170 identifies information for all available lots of an analyte. The table includes a system lot number field 170-1, an OEM number field 170-2, an OEM lot number field 170-3, a level identification field 170-4, an expiration date field 170-5, and a product name field 170-6. The system lot number is a unique number generated by the system automatically to distinguish between two different quality control products having the same lot number. The lots table 170 is linked forward to the customer product lot table 140, the package insert table 160 and the lot analyte table 180 via the system lot number field 170-1.

The lot analyte table 180 stores all of the allowable analytes that a particular quality control product (or lot number) is capable of having, such as the range of expected values that a particular analyte lot is capable of reporting. The table includes a system lot number field 180-1, an analyte identification field 180-2, a mean high value field 180-3, a mean low value field 180-4, and a standard deviation high value field 180-5. It is understood that the standard deviation can never be less than 0 (the low value). The lot analyte table 180 links back to the lots table 170 and forward to the package insert table 160 via the system lot number field 180-1. The lot analyte table 180 intersects with the product analyte table 150 and the package insert table 160 to ascertain the total allowable analytes that can be reported on a particular analyzer using a specific lot of controls.

The cumulative data table 190 is a master data table and stores the cumulative entered data for a particular analyte as related to a particular control lot for a particular analyzer for a particular customer. The table includes a customer product number field 190-1, a system lot number field 190-2, a date field 190-3, a level identification field 190-4, an analyte identification field 190-5, a points field 190-6 for identifying the number of data points represented by the cumulative data, a units field 190-7 for specifying the units of measure, a mean value field 190-8, and a standard deviation value field 190-9. Also shown are a readings field 190-10, an accept flag 190-11, a reject flag 190-12, and an out-of-range flag 190-13. The cumulative data table 190 links back with the customer product table 120 via the customer product number field 190-1.

Figure 3A:
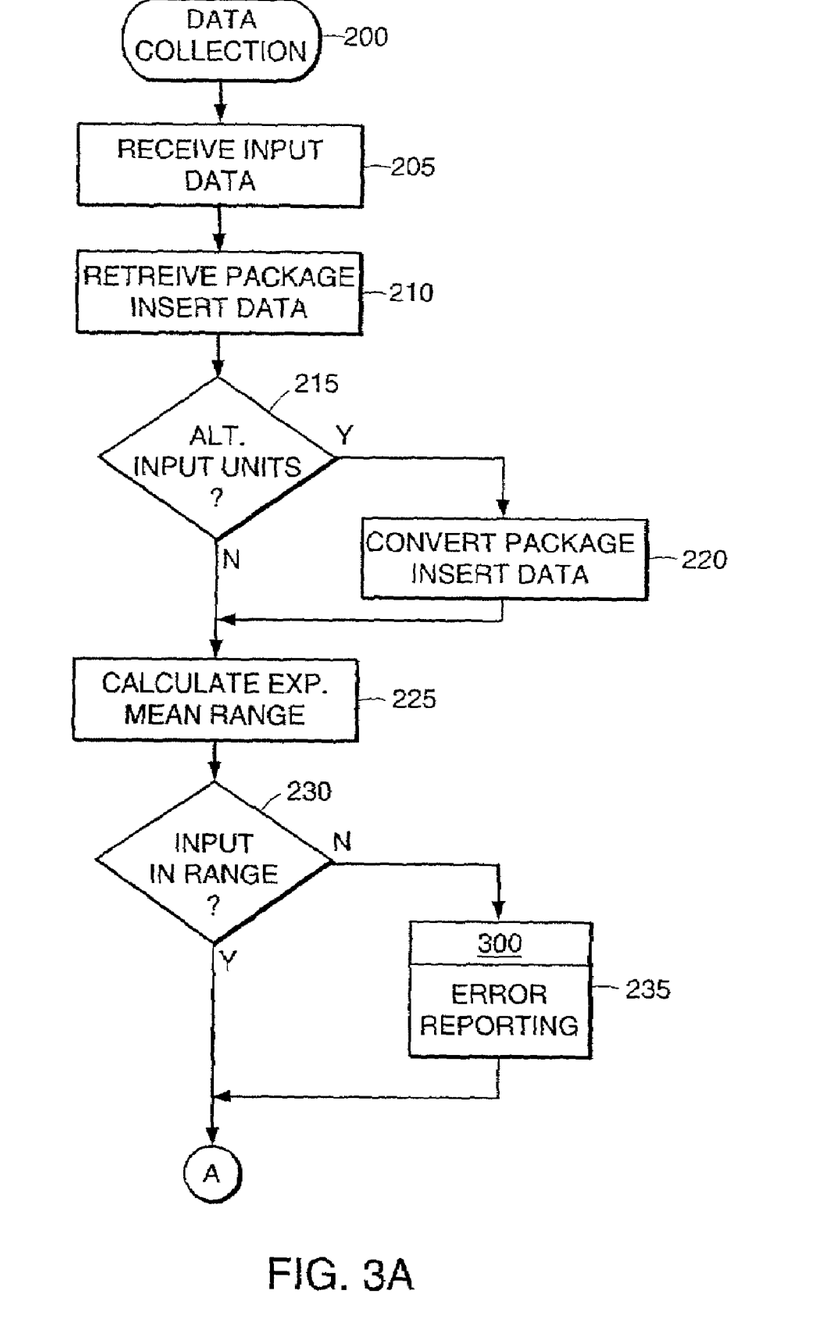
FIGS. 3A–3B are a flowchart of a particular error checking module 13 of FIG. 1.
Figure 3B:
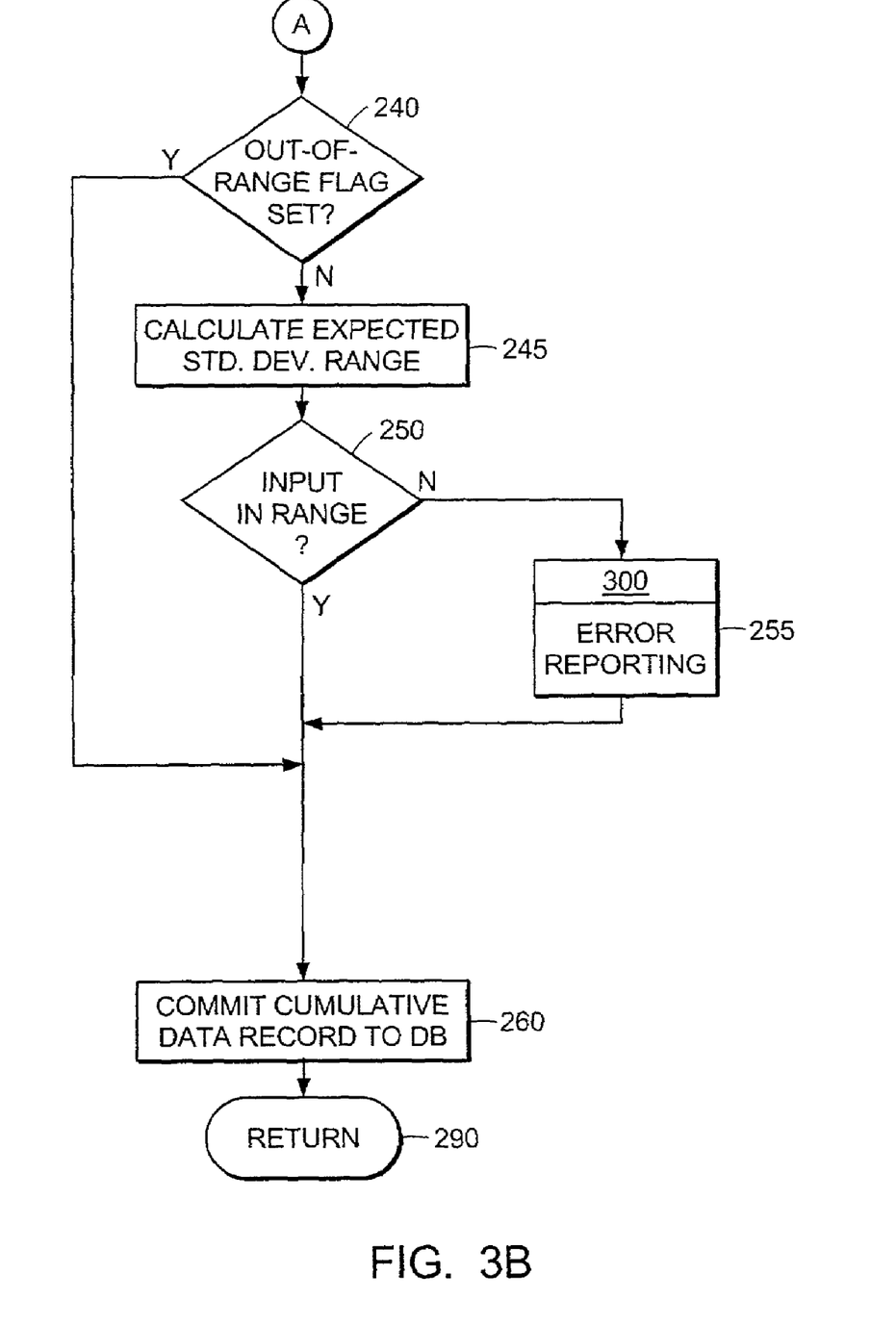

FIGS. 3A–3B are a flowchart of a particular error checking module 13 of FIG. 1. Referring to FIG. 3A, the error checking processing flow 200 begins at step 205, where the input data is received. At step 210, the program retrieves the analyzer and analyte lot data from the package insert table.

At step 215, the input data is checked for alternate units of measure. If alternate units of measure are used, processing proceeds to step 220, where the package insert data is converted to the alternate units. Processing then continues to step 225.

At step 225, a mean range is calculated from the package insert data. At step 230, the entered mean input data is verified against a mean range. The mean range is defined as the value of the mean field 160-4 (taking into consideration any conversion) plus or minus twice the value of the standard deviation field 160-5. If the data is within the mean range, processing continues to step 240; otherwise processing continues to step 235 where an error reporting routine 300 is called. Upon return from the error reporting routine, processing continues to step 240.

At step 240, in FIG. 3B, the out-of-range flag 190-13 (FIG. 2) is checked. If the flag is set, processing jumps to step 260. If the flag is not set, processing continues to step 245, where a standard deviation range is calculated from the package insert data. The standard deviation range is defined as between 0 and twice the stored value in the standard deviation field 160-5.

At step 250, the entered standard deviation data is verified against the calculated value. If the entry is within range, processing continues to step to 260. If the input data is not verified, processing continues to step 255 where the error processing routine 300 is invoked. Upon return for the error processing routine, processing continues to step 260.

At step 260, the cumulative data is committed to a cumulative data record in the database. The value of the out-of-range flag 190-13 will establish if the record is included in reports. Processing then continues to step 290, where the error checking flow completes and processing returns to the calling program.

Figure 4:
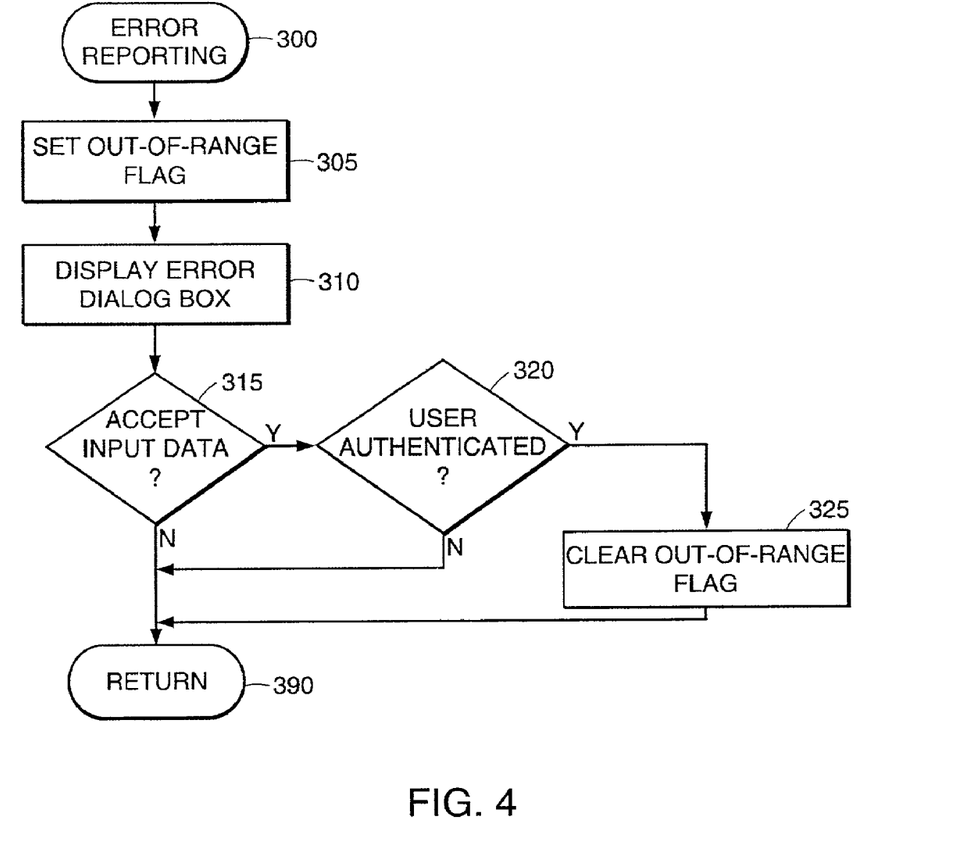
FIG. 4 is a flowchart of the error reporting routine 300 of FIG. 3.

FIG. 4 is a flowchart of the error reporting routine 300 of FIG. 3. The error reporting processing flow 300 begins at step 305, where the out-of-range flag 190-13 (FIG. 2) is set to indicate an error in the input data. Then, at step 310, an error message dialog box is displayed to the user. At step 315, the user can choose to accept the input data. If the user chooses to accept the input data processing continues to step 320; otherwise continues to step 390.

At step 320, the user's authority is verified. If the user is not authorized to accept the data, processing continues to step 390; otherwise processing continues to step 325.

At step 325, the out-of-range flag 190-13 is cleared to indicate that the data is valid. Processing then continues to step 390.

At step 390, processing returns to the calling program.

New data can be entered into the database as either raw data or cumulative data. That is, an operator can enter a plurality of individual data points and rely on the data collection program to compute the cumulative mean and standard deviation values. The raw values, however, need not be stored in the database. An operator can alternatively perform the mean and standard deviation calculations and enter the results, instead of the raw data. In either case, the mean and standard deviation values are checked for errors.

Figure 5:
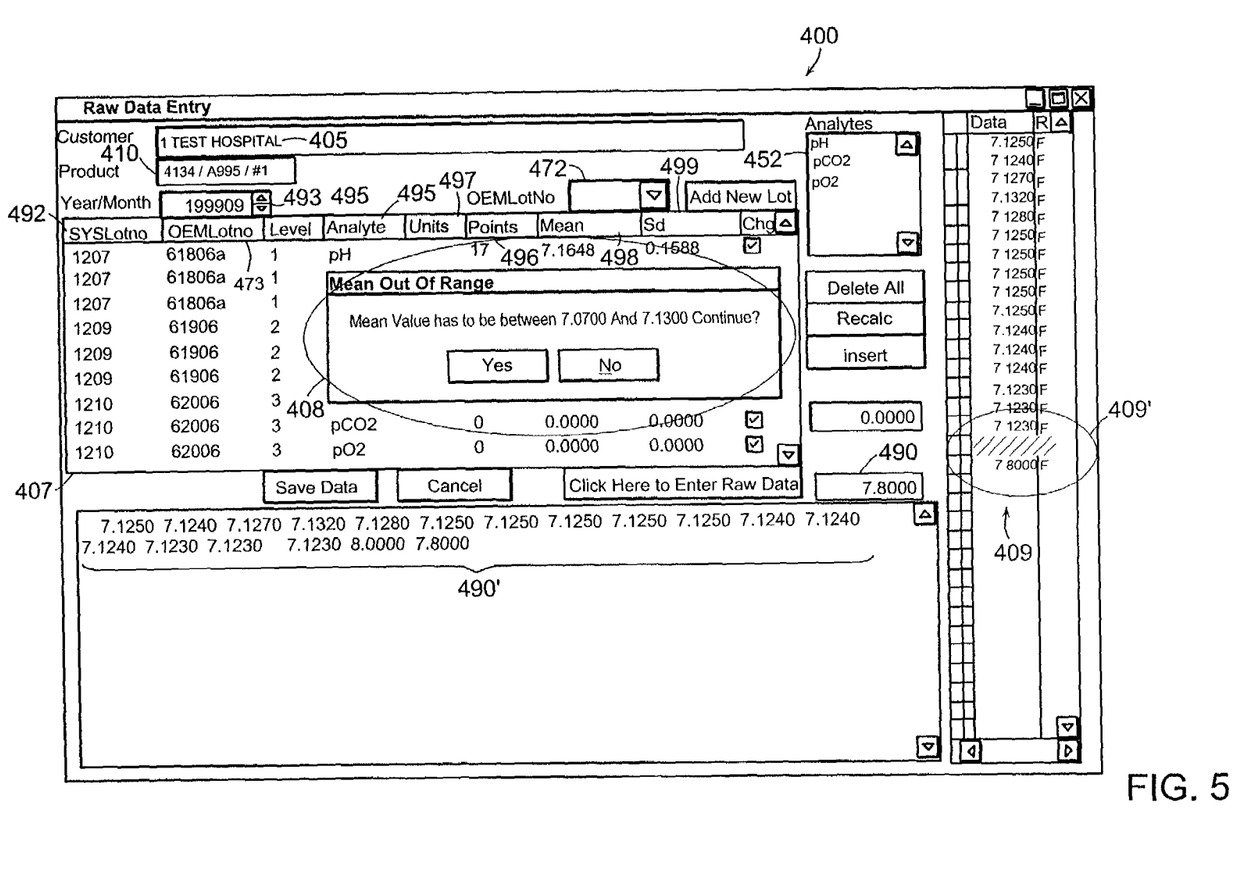
FIG. 5 is a display view of a particular raw data entry form.

FIG. 5 is a display view of a particular raw data entry form. Shown are a plurality of input fields, including a customer input field 405, a product input field 410, a date input field 493, an OEM lot number field 470, and a raw data entry field 490. The customer data entry field 405 corresponds to data in the customer table 100 (FIG. 2). The product data entry field 410 corresponds to the product table data 110. The data entry field 493 corresponds to the date field 190-3. The OEM lot number field 470 is used by the operator to input a new lot corresponding to a new record in the lots table record 170. Values for individual data points can be entered individually via the data entry field 490 or as a space-delimited list via a list entry field 490'. A list of entered data point values is displayed at 409.

A display window 407 presents, to the operator, data from the cumulative data table 190 (FIG. 2) that corresponds to the selected customer, product, and date. Each column of the display window 407 corresponds to a data field derived from the cumulative data table 190 and each row corresponds to a record in the cumulative data table 190. In particular, there is a system lot number column 492, an OEM lot number column 473, a level column 494, an analyte column 495, a units column 497, a data points column 496, a mean value column 498, and a standard deviation value column 499.

As shown, one of the data points has caused the mean value to go out of range. This results in a dialog box 408 being displayed to the user and the out-of-range data point being highlighted 409'. The user has the option or accepting or rejecting that data point. As shown there are seventeen data points applied in calculating the mean and standard deviation values.

Figure 6:
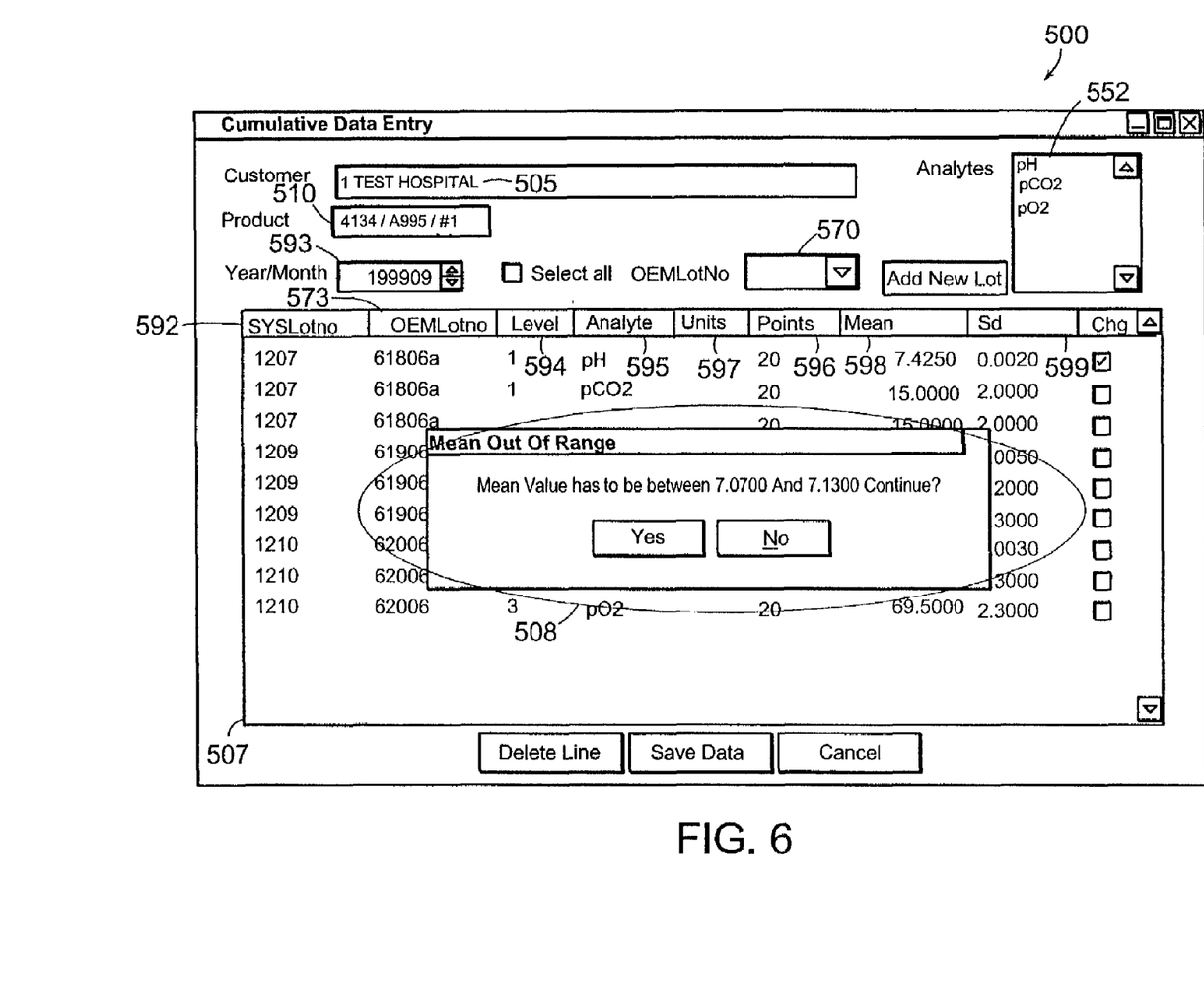
FIG. 6 is a display view of a particular cumulative data entry form.

FIG. 6 is a display view of a particular cumulative data entry form. Note that the cumulative data entry form 500 shares some features with the raw data entry form 400 of FIG. 5. In particular, there is a customer data entry field 505, a product selection field 510, a data selection field 593, an OEM lot number selection field 570. There is also a display window 507 which displays cumulative data for the selected customer, product, and date.

The display window 507 presents, to the operator, data from the cumulative data table 190 (FIG. 2) that corresponds to the selected customer, product, and date. Each column of the display window 507 corresponds to a data field derived from the cumulative data table 190 and each row corresponds to a record in the cumulative data table 190. In particular, there is a system lot number column 592, an OEM lot number column 573, a level column 594, an analyte column 595, a units column 597, a data points column 596, a mean value column 598, and a standard deviation value column 599.

Unlike the raw data entry form 400 of FIG. 5, the cumulative data entry form 500 of FIG. 6 accepts only cumulative data. As shown, the user enters cumulative mean values through a data entry field 509. A similar data entry field is provided for entry other data for the table record. As shown, a dialog box 508 indicates that the entered mean value is out of range. Note that the user can elect to accept or reject the entered value. Similar processing occurs for entry of the standard deviation values.

After data has been entered into the database, reports can be generated by querying the database through the reporting module 14 of FIG. 1.

Figure 7:
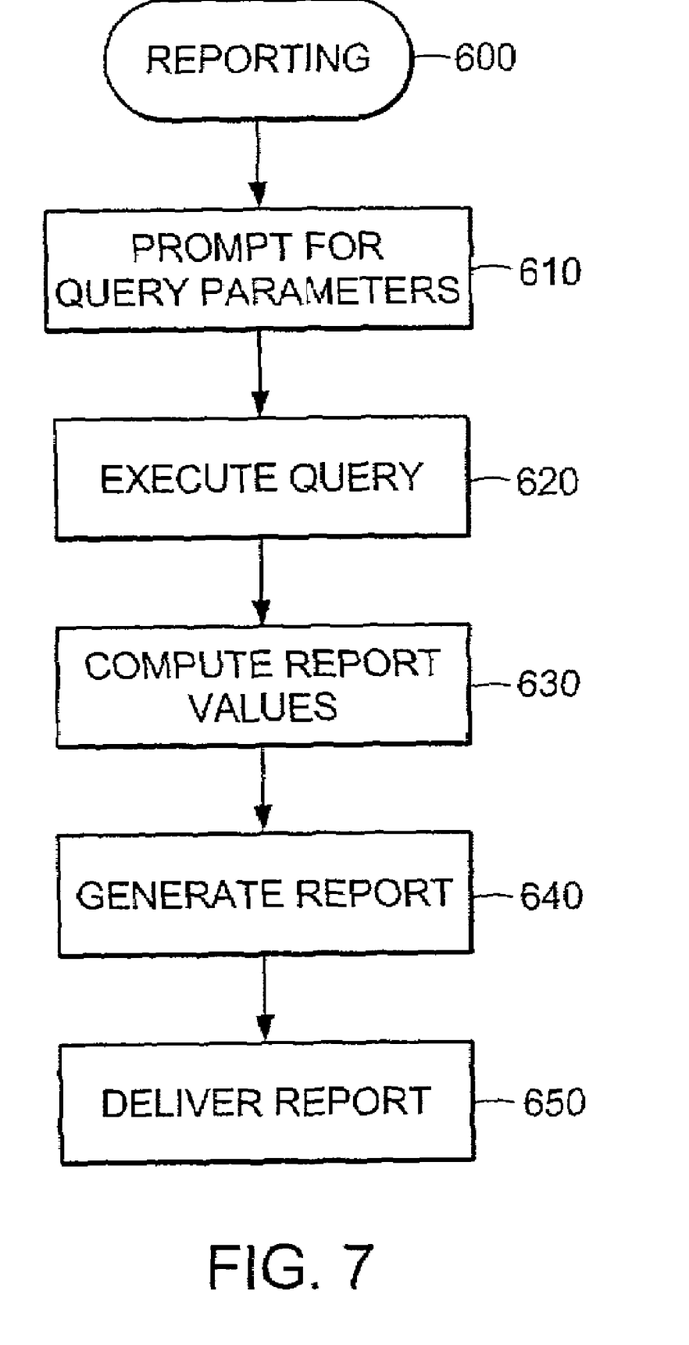
FIG. 7 is a flowchart of a particular reporting module 14 of FIG. 1.

FIG. 7 is a flowchart of a particular reporting module 14 of FIG. 1. The reporting process flow 600 begins at step 610, where a user is prompted for query parameters. These parameters can include dates, individual customers, specific instruments, specific analytes, etcetera.

In a particular embodiment, the user can generate a report based on a peer group. Peer groups can be viewed as a short-hand categorization of query parameters. For example, peer group can be defined to filter data based on the type of customer, e.g. commercial laboratory, hospital laboratory, or research laboratory. The peer group can also be used to filter data based on location of a laboratory. The peer group can also be used to filter the data based on the equipment manufacturer, equipment model, or equipment maintenance contractor. Other peer groups can also be defined.

At step 620, a query is executed against the database based on the entered parameters. The query results are processed, at step 630, to compute values for the report. Many values provided on the report are calculated from the cumulative data. In particular, coefficient of variance (CV), coefficient of variance index (CVI), and standard deviation index (SDI) values are computed. Other statistical calculations can be made in addition to, or substituted for, these computed statistical measures.

After all the report values are computed, the report is generated at step 640. This step involves formatting the data as specified by the user. The generated reports can be delivered to recipient at step 650, such as printing a hard copy or electronically transmitting the report.

FIG. 8 illustrates an example report generated by the reporting function 600 of FIG. 7. The report 700 includes statistical data for a particular date 710, cumulative statistics 720, and peer group statistics 730. The report has been generated for a particular model of a Radiometer™ blood gas analyzer 705. From the report, the performance of the particular instrument can be evaluated.

The monthly statistics 710 are generated for the particular instrument. They include the number of accepted data points 711, the number of rejected data points 712, the mean data values 713, and standard deviation data values 714 as recorded in the database 16 (FIG. 1). Also shown are computed values for twice the standard deviation range 716, the CV percentage 717, and the SDI 718.

The cumulative statistics 720 are also generated for the particular instrument. They include the number of data points 721, the mean data values 723, and standard deviation data values 724 as recorded in the database 16 (FIG. 1). Also shown are computed values for twice the standard deviation range 726, the CV percentage 727, and the SDI 728. By comparing the cumulative statistics with the monthly statistics, one can gauge deviations from the cumulative data.

The peer group contains certain models of Radiometer™ blood gas analyzers. The peer group statistics 730 include the number of data points 731, the mean data values 733, and standard deviation data values 734 as recorded in the database 16 (FIG. 1). Also shown are computed values for the CV percentage 737, and the coefficient of variance index (CVI) 738. By comparing the peer group statistics with the monthly and cumulative statistics, one can gauge the performance of the particular instrument with others in the selected peer group.

Those of ordinary skill in the art should recognize that methods for implementing a system for statistical analysis of analytes and instrumentation data may be embodied in a computer program product that includes a computer usable medium. For example, such a computer usable medium can include a readable memory device, such as a solid state memory device, a hard drive device, a CD-ROM, a DVD-ROM, or a computer diskette, having computer-readable program code segments stored thereon. The computer readable medium can also include a communications or transmission medium, such as a bus or a communications link, either optical, wired, or wireless, having program code segments carried thereon as digital or analog data signals.

While the system has been particularly shown and described with references to particular embodiments thereof, it will be understood by those of ordinary skill in the art that various changes in form and details may be made therein without departing from the scope of the invention encompassed by the appended claims. For example, the methods of the invention can be applied to various environments, and are not limited to the environment described herein. In particular, aspects of the invention may be employed for testing other types of analyzers beyond chemical analyzers, including but not limited to devices that measure physical properties. Such properties include electromagnetic properties, such as electromagnetic fields, and radioactivity.

What is claimed is:

1. A computer system for evaluating the performance of a quantitative analyzer relative to a group of quantitative analyzers, the quantitative analyzer capable of measuring the composition of a test analyte having an expected composition, comprising:
    a database having stored therein, for a plurality of quantitative analyzers, statistical data for the test analyte, including expected statistical data representing the expected composition of the test analyte;
    a computer coupled to the database and to a communication network;
    a data collection module in the computer for electronically receiving data from the communication network representing a measured composition of the test analyte from a quantitative analyzer for storage into the database; and
    an error checking module in the computer for comparing the received data with the expected composition in real time with the receipt of the received data by the data collection modules wherein the error checking module includes an error reporting function for reporting, in real time to a remote user over the communication network, received data outside a range of expected data for the expected composition and the error reporting function is capable of receiving a corrected data value from the user for entry storage into the database.

2. The computer system of claim 1, wherein the expected statistical data is specific to a control lot of the test analyte.

3. The computer system of claim 1, wherein the expected statistical data is specific to a particular quantitative analyzer model.

4. The computer system of claim 1, wherein the statistical data includes a mean data value and a standard deviation data value.

5. The computer system of claim 1, wherein the data collection module receives data from a communication network coupled between the computer and the quantitative analyzer.

6. The computer system of claim 5, wherein the received data is electronically transmitted over the communication network by the quantitative analyzer.

7. The computer system of claim 5, wherein the received data is electronically transmitted over the communication network by a remote computer coupled to the quantitative analyzer.

8. The computer system of claim 1, wherein the database has stored therein cumulative statistical data for the quantitative analyzer 9. The computer system of claim 1, further comprising a reporting module for generating query reports.

10. The computer system of claim 9, wherein the reporting module is capable of generating reports based on a peer group selected by a user.

11. The computer system of claim 9, wherein the query report is available in real time.

12. The computer system of claim 11, wherein the query report is accessible over the communication network.

13. A computer system for evaluating the performance of a quantitative analyzer relative to a group of quantitative analyzers, the quantitative analyzer capable of measuring the composition of a test analyte having an expected composition, comprising:
    a database having stored therein, for a plurality of quantitative analyzer models, statistical data for a test analyte, including expected statistical data representing the expected chemical composition of the test analyte, the expected statistical data being specific to the quantitative analyzer model and to a control lot of The test analyte;
    a computer coupled to the database and to a communication network;
    a data collection module in the computer for electronically receiving from the communication network data representing a measured composition of the test analyte from a quantitative analyzer under test for storage into the database;
    an error checking module in the computer for comparing the received data with the expected composition in real time with the receipt of the received data by the data collection module, wherein the error checking module includes an error reporting function for reporting, in real time to a remote user over the communication network, received data outside a range of expected data for the expected composition and the error reporting function is capable of receiving a corrected data value for storage into the database; and
    a report generation module in the computer for generating reports from the statistical data stored in the database.

14. The computer system of claim 13, wherein the data collection module receives data from a manual user input.

15. The computer system of claim 13, wherein the statistical data includes a mean data value and a standard deviation data value.

16. The computer system of claim 13, wherein the communication network is coupled between the computer and the quantitative analyzer under test.

17. The computer system of claim 16, wherein the received data is electronically transmitted over the communication network by the quantitative analyzer under test.

18. The computer system of claim 16, wherein the received data is electronically transmitted over the communication network by a remote computer coupled to the quantitative analyzer under test.

19. The computer system of claim 13, wherein the database has stored therein cumulative statistical data for a plurality of quantitative analyzers, including the quantitative analyzer under test.

20. The computer system of claim 13, wherein the reporting module is capable of generating reports based on a peer group selected by a user.

21. The computer system of claim 13, wherein the report is available in real time.

22. The computer system of claim 21, wherein the report is accessible over the communication network.

23. The computer system of claim 13, wherein the error checking module detects a human-induced error in the received data.

24. The computer system of claim 13, wherein the expected composition has a first unit of measure and the measured composition has a second unit of measure.

25. The computer system of claim 24 wherein the error checking module converts the first unit of measure to the second unit of measure and the generated report uses the second unit of measure.

26. A computer-implemented method for evaluating the performance of a quantitative analyzer relative to a group of quantitative analyzers using a test analyte having an expected composition, the quantitative analyzer capable of measuring the composition of the test analyte, comprising:
for a plurality of quantitative analyzers, storing statistical data for a test analyte, including expected statistical data representing the expected composition of the test analyte, in a database;
in a computer coupled to the database and to a communication network:
from the communication network, electronically receiving data representing a measured composition of the test analyte from quantitative analyzer;
comparing the received data with the expected composition and reporting, to a remote user over the communication network, received data outside a range of expected data for the expected composition in real time with the receiving, of the received data; and
receiving a corrected data value for storage into the database.

27. The method of claim 26, wherein the expected statistical data is specific to a control lot of the test analyze.

28. The method of claim 26, wherein the expected statistical data is specific to a particular quantitative analyzer model.

29. The method of claim 26, wherein the statistical data includes a mean data value and a standard deviation data value.

30. The method of claim 26, wherein receiving comprises receiving data from a communication that is coupled between the computer and the quantitative analyzer.

31. The method of claim 30, wherein the received data is electronically transmitted over the communication network by the quantitative analyzer.

32. The method of claim 30, wherein the received data is electronically transmitted over the communication network by a remote computer coupled to the quantitative analyzer.

33. The method of claim 26, wherein storing comprises storing cumulative statistical data for the quantitative analyzer in the database.

34. The method of claim 26, further comprising generating query reports.

35. The method of claim 34, wherein generating query reports comprises generating reports based on a peer group selected by a user.

36. The method of claim 34, wherein the query report is available in real time.

37. The method of claim 36, wherein the query report is accessible over the communication network.

38. A computer-implemented method of evaluating the performance of a quantitative analyzer relative to a group of quantitative analyzers for a test analyte having an expected composition, a quantitative analyzer under test capable of measuring the composition of the test analyte, comprising:
for a plurality of quantitative analyzer models, storing statistical data for a rest analyte in a database, including storing expected statistical data representing the expected composition of the test analyte, the expected statistical data being specific to the quantitative analyzer model and to a control lot of the test analyte;
in a computer coupled to the database and to a communication network:
from the communication network, electronically receiving data representing a measured composition of the test analyte from a quantitative analyzer under test;
comparing the received data with the expected composition in real time with receiving of the received data;
generating reports from the statistical data stored in the database;
reporting to a remote user over the communication network received data outside a range of expected data for the expected composition in real time with the comparing of the received data with the expected composition and
receiving a corrected data value for entry into the database.

39. The method of claim 38, wherein receiving comprises receiving data from a manual user input.

40. The method of claim 38, wherein the statistical data includes a mean data value and a standard deviation data value.

41. The method of claim 38, wherein receiving comprises receiving data from a communication network that is coupled between the computer and the quantitative analyzer under test.

42. The method of claim 41, wherein the received data is electronically transmitted over the communication network by the quantitative analyzer under test.

43. The method of claim 41, wherein the received data is electronically transmitted over the communication network by a remote computer coupled to the quantitative analyzer under test.

44. The method of claim 38, wherein storing comprises storing cumulative statistical data for a plurality of quantitative analyzers, including the quantitative analyzer under test.

45. The method of claim 38, further comprising, in the computer, generating reports based on a peer group selected by a user.

46. The method of claim 38, wherein the report is available in real time.

47. The method of claim 46, wherein the report is accessible over the communication network.

48. The method of claim 38, wherein comparing comprises detecting a human-induced error in the received data.

49. The method of claim 38, wherein the expected composition has a first unit of measure and the measured composition has a second unit of measure.

50. The method of claim 49, wherein comparing comprises converting the first unit of measure to the second unit of measure, and wherein generating comprises using the second unit of measure in the report.

51. An article of manufacture, comprising:
a computer-usable medium;
a set of computer instructions carried on the medium including instructions for a computer-implemented method for evaluating the performance of a quantitative analyzer relative to a group of quantitative analyzers using a test analyte having an expected composition, the quantitative analyzer capable of measuring the composition of the test analyte, the method including instructions to:
for a plurality of quantitative analyzers, store statistical data for a test analyte, including expected statistical data representing the expected composition of the test analyte, in a database,
in a computer coupled to the database and to a communication network:
from the communication network, electronically receive data representing a measured composition of the test analyte from a quantitative analyzer;
in real time with receipt of the received data, compare the received data with the expected composition and reporting to a remote user over the communication network received data outside a range of expected data for the expected composition; and
receive a corrected data value for storage into the database.

52. An article of manufacture, comprising:
a computer-usable medium;
a set of computer instructions carried on the medium, including instructions for a computer-implemented method of evaluating the performance of quantitative analyzer relative to a group of quantitative analyzers for a test analyte having an expected composition, a quantitative analyzer under test capable of measuring the composition of the test analyte the method including instructions to:
for a plurality of quantitative analyzer models, store statistical data for a test analyte in a database, including storing expected statistical data representing the expected composition of the test analyte, the expected statistical data being specific to the quantitative analyzer model and to a control lot of the test analyte;
in a computer coupled to the database and to a communication network:
from the communication network, electronically receive data representing a measured composition of the test analyte from a quantitative analyzer under test;
compare the received data with the expected composition in real time with he receipt of the received data;
generate reports from the statistical data stored in the database;
report to a remote user over the communication network received data outside a range of expected data for the expected composition in real time; and
receive a corrected data value for storage into the database.

53. A computer system for evaluating the performance of a quantitative analyzer relative to a group of quantitative analyzers, the quantitative analyzer capable of measuring the composition of a test analyte having an expected composition, comprising:
a database having stored therein, for a plurality of quantitative analyzers statistical data for a test analyte, including expected statistical data representing the expected composition of the test analyte, the expected statistical data for the test analyte is cumulative over time and capable of being associated with a peer group of the quantitative analyzers;
a computer coupled to the database and to a communication network;
a data collection module in the computer for electronically receiving from the communication network data representing a measured composition of the test analyte from a quantitative analyzer for storage into the database; and
an error checking module in the computer and responsive to the data collection module for comparing the received data with the expected statistical data of the expected composition in real time and excluding the received data from association with the peer group of the quantitative analyzers if the received data is outside a range of expected data for the expected composition, wherein the error checking module includes an error reporting function for reporting to a remote user, over the communication network in real time, received data outside the range of expected data for the expected composition.

* * * * *